US011472752B2

(12) United States Patent
Castro Cabrera

(10) Patent No.: US 11,472,752 B2
(45) Date of Patent: Oct. 18, 2022

(54) METHOD FOR MAKING RESISTANT TO THIODICARB (CARBAMATE) AND BIFENTHRIN (PYRETHROID) A CONSORTIUM OF FUNGI THAT SOLUBILISE PHOSPHOROUS AND ANTAGONISE CERTAIN PATHOGENS, FOR USE IN LIQUID BIOFERTILISERS FOR FOLIAR AND/OR SOIL APPLICATION

(71) Applicant: Salus Mundi Investments Limited, Mexico City (MX)

(72) Inventor: Luis Orlando Castro Cabrera, Mexico City (MX)

(73) Assignee: Salus Mundi Investments Limited, Mexico City (MX)

( * ) Notice: Subject to any disclaimer, the term of this patent is extended or adjusted under 35 U.S.C. 154(b) by 54 days.

(21) Appl. No.: 16/619,193

(22) PCT Filed: Jan. 30, 2019

(86) PCT No.: PCT/MX2019/000007
§ 371 (c)(1),
(2) Date: Dec. 4, 2019

(87) PCT Pub. No.: WO2019/160401
PCT Pub. Date: Aug. 22, 2019

(65) Prior Publication Data

US 2020/0113188 A1 Apr. 16, 2020

(30) Foreign Application Priority Data

Feb. 19, 2018 (MX) .................. MX/A/2018/002087

(51) Int. Cl.
*C05F 11/08* (2006.01)
*A01N 63/38* (2020.01)
*A01N 63/30* (2020.01)

(52) U.S. Cl.
CPC .............. *C05F 11/08* (2013.01); *A01N 63/30* (2020.01); *A01N 63/38* (2020.01)

(58) Field of Classification Search
CPC .......... A01N 63/30; A01N 63/38; C05F 11/08
USPC ........................................................ 424/93.5
See application file for complete search history.

(56) References Cited

U.S. PATENT DOCUMENTS

| | | | |
|---|---|---|---|
| 4,952,229 | A | 8/1990 | Muir |
| 2011/0151508 | A1 | 6/2011 | Lopez-Cervantes et al. |
| 2011/0306116 | A1* | 12/2011 | Jin ......................... B01J 13/043 435/254.1 |
| 2012/0329650 | A1 | 12/2012 | Lopez-Cervantes |
| 2013/0255338 | A1 | 10/2013 | Lopez-Cervantes et al. |
| 2014/0212387 | A1* | 7/2014 | Luth ...................... A01N 63/30 424/93.4 |
| 2016/0100587 | A1 | 4/2016 | Bywater-Ekegard et al. |

FOREIGN PATENT DOCUMENTS

| | | |
|---|---|---|
| MX | PA06003777 | 10/2008 |
| MX | 347762 | 11/2017 |
| WO | 2013148278 | 10/2013 |

OTHER PUBLICATIONS

Krauss et al., Interaction Between the Entomopathogens Beauveria bassiana, Metarhizium anisopliae and Paecilomyces fumosoroseus and the *Mycoparasites clonostachys* spp., Trichoderma harzianum and Lecanicillium lecanii, Biocontrol Science and Technology, vol. 14, Issue 4, (2010), pp. 331-346.*
English Abstract of Colombian Patent No. 26662—1997
Orozco-Jaramillo, J. C. et al.,"Test of the seeding of nitrogen-fixing non-symbiotic microorganisms isolated from the rhizosphere of Pinus patula in Colombia," Alexander von Humboldt Biological Research Institute, La Florida Forest Station, Cota, Cundinamarca-Colombia, 2009, Bosque 30(2): 70-77.
Cuervo Lozado, J., "Isolation and Characterization of the *Bacillus* spp as biological nitrogen fixers and phosphate solubilizers in two samples of commercial biofertilizers," Dissertation, Pontificia Universidad Javeriana, Bogotá, Colombia, 2010.
Kabir, M. et al., "Identification of Azospirillum by oligonucleotide probes after isolation from soil and Sourghum rizoplan contaminated or not by the parasitic plant Siriga," Advances in Applied Microbiology, 1995, vol. 35, pp. 195-253.
Kabir, M. et al., "Oligonucleotide probes based on 16S rRNA sequences for the identification of four Azospirillum species," 1995, Can. J. Microbiol., 41: 1081-1087.
Validation of the Publication of New Names and New Combinations Previously Effectively Published Outside the IJSB, List No. 51, International Journal of Systematic Bacteriology, 1994.
Rivas, N. et al., "Bacterias promotoras del crecimiento vegetal en el cultivo del arroz (*Oryza sativa* L.). Perspectivas de su uso en Cuba," 2007, Cultivos Tropicales, vol. 28, No. 2, pp. 29-38.
Cycon, M. et al., "Pyrethroid-degrading microorganisms and their potential for the bioremediation of contaminated soils: a review," 2016, Frontiers in Microbiology , vol. 7, Article No. 1463.
Afshan, N-U-S et al., "Pesticide tolerant plant growth promoting rhizobacteria isolated from rhizosphere of okra," 2015, Soil Environ., vol. 34(2), pp. 111-118 (Abstract).

(Continued)

*Primary Examiner* — Jennifer M. H. Tichy
(74) *Attorney, Agent, or Firm* — Preston Smirman; Smirman IP Law, PLLC

(57) ABSTRACT

The present invention provides a method for making a consortium of fungi resistant to traces of carbamates contained in thiodicarb and to traces of synthetic pyrethroids contained in bifenthrin. During the course of this research, carried out over more than five years, the strains were subjected to a change in physical medium, adapting same to tolerate increasing concentrations of thiodicarb and bifenthrin. This compound enriches and increases the concentration of beneficial microorganisms, generating high-quality liquid biological fertilisers suitable for use in agricultural production, in land recovery and conservation, under the parameters established in sustainable organic farming, which seeks to conserve, recover and use nature or the environment without generating the least negative impact.

4 Claims, No Drawings

(56) References Cited

OTHER PUBLICATIONS

Ahmed, M. et al., "Analysis of bifenthrin degrading bacteria from rhizosphere of plants growing at tannery solid waste, " 2015, American Journal of Plant Sciences, vol. 6, pp. 2042-2050.
Roy, T. et al., "Isolation, characterization and identification of two methomyl-degrading bacteria from a pesticide-treated crop field in West Bengal, India," 2017, Microbiology, vol. 86(6), pp. 753-764.
McClure, G. W. et al., "Degradation on phenylcarbamates in soil by mixed suspension of IPC-adapted microorganism," 1972, J. Environ. Quality, vol. 1(2), pp. 177-180.
Gong, T. et al., "An engineered Pseudomonas putida can simultaneously degrade organophosphates, pyrethroids and carbamates," 2018, Science of the Total Environment, vol. 628-629, pp. 1258-1265.
Asi, M. R. et al., "Compatability of entomorpathogenic fungi, Metarhizium anisopliae and Paecilomyces fumosoroseus with selective insecticides," 2010, Pakistan Journal of Botany, vol. 42(6), pp. 4207-4214.
Mohammadi, A. Y. et al., "The influence of pesticides and herbicides on the growth and spore gemrination of Trichoderma harzianum," 2015, Agriculture Science Development, vol. 4(3), pp. 41-44.
Abidin, A. F. et al., "Insecticide compatibility to the entomopathogenic fungi Beauveria bassiana and Metarhizium anisopliae," 2017, Scripta Biologica, vol. 4(4), pp. 273-279.
Thube, S. H. et al., "Compatability study of insecticides recommended for the management of tea mosquito bug *Helopeltis* spp. with bio-fungicide, Trichoderma harzianum," 2018, Journal of Entomology and Zoology Studies, vol. 6 (5), pp. 2034-2039.
English Abstract of Colombian Patent No. 4650219—Published 1998.
International Search Report for PCT/MX2019/000005 dated Jun. 27, 2019.
International Search Report for PCT/MX2019/000007 dated Jun. 27, 2019.
International Search Report for PCT/MX2019/000006 dated Jun. 27, 2019.
Written Opinion of the International Searching Authority for PCT/MX2019/000005 dated Jun. 27, 2019.
Written Opinion of the International Searching Authority for PCT/MX2019/000007 dated Jun. 27, 2019.
Written Opinion of the International Searching Authority for PCT/MX2019/000006 dated Jun. 27, 2019.
International Preliminary Report on Patentability for PCT/MX2019/000005 dated Aug. 27, 2020.
International Preliminary Report on Patentability for PCT/MX2019/000007 dated Aug. 27, 2020.
International Preliminary Report on Patentability for PCT/MX2019/000006 dated Aug. 27, 2020.
Corrales, L. C. et al., "Efecto Biocontrolador de '*Bacillus*' spp., Frente a '*Fusarium*' sp., Bajo Condiciones de Invernadero en Plantas de Tomillo ('*Thymus Vulgaris l*'.)," 2012, Nova, vol. 10(17), pp. 64-82.

* cited by examiner

METHOD FOR MAKING RESISTANT TO THIODICARB (CARBAMATE) AND BIFENTHRIN (PYRETHROID) A CONSORTIUM OF FUNGI THAT SOLUBILISE PHOSPHOROUS AND ANTAGONISE CERTAIN PATHOGENS, FOR USE IN LIQUID BIOFERTILISERS FOR FOLIAR AND/OR SOIL APPLICATION

CROSS-REFERENCE TO RELATED APPLICATION

The instant application is a national phase of PCT International Patent Application Serial No. PCT/MX2019/000007 filed Jan. 30, 2019, and claims priority to Mexican Patent Application Serial No. MX/a/2018/002087 filed Feb. 19, 2018, the entire specifications of both of which are expressly incorporated herein by reference.

1. INVENTION BACKGROUND

Since the TECHNIQUE STATUS regarding the scientific investigation and application of technology targeted to induce growth, repopulation and development of a consortium of beneficial microorganisms that can tolerate trace chemicals on soils and organic residues, and that are resistant to new generations of substances replacing conventional agrochemicals (forbidden in agriculture), is stated mainly in PATENT No. PA/2006/003777, issued by the IMPI (Apr. 27, 2017) where consortia of microorganisms resistant to organochlorinated and organophosphate compounds were isolated, in this new request we describe the intent to develop an INVENTIVE ACTIVITY to develop, grow and select consortia of fungi resistant to chemical compounds in new generations of pesticides and biological control such as pyrethroid and carbamate compounds that are supposed to have a controlled use because of their secondary effects that pollute the soils, water mantles, and effect on agricultural development.

The information submitted this document, the INNOVATION is formed by developing a consortium of specific fungi species, adapted to resist, tolerate and mineralize the organic matter polluted with carbamate such as thiodicarb and pyrethroids such as bifenthrin, these compounds are currently used in the agricultural and livestock industries, and are present in the organic residues, which are not usually exploited and generate pollution such as horse manure, dairy residues, pancreatic enzymes, carbohydrates, etc.; this consortium enriches them and a fungal micro load is obtained, which, when applied to crops, the phosphorous available in soils is dissolved as $P_2O_4$ by adding one O and turning it into $P_2O_5$ available to be used by plants, it contains antagonists to some pathogens and repopulates the soil with beneficial fungi. It is worth mentioning that the microorganisms forming our consortia ARE NOT GENETICALLY MODIFIED nor are human, animal or plant pathogens.

With the use of organochlorinated and organophosphate compounds banned as pesticides on the second half of the twentieth century, carbamate and pyrethroid compounds become an alternative. Carbamate are pesticide substances formed by a N atom bonded to a labile group, the carbamic acid; its main characteristic is its high toxicity, low chemical stability and null build up on tissues; and pyrethroids are molecules with pesticide activity, they remain longer in the environment because the chemical modification of their formula makes them more stable under sunlight and to heat.

These products are used indiscriminately in the agricultural and livestock industries, generating residues.

This research is outlined within the guidelines of the United Nation's Agenda 21 (Chapters 10, 11, 12 and 14, accordingly), regarding desertification and drought; agriculture and sustainable development. Calculations show that soil degradation on a world scale extends over 2000 millions of hectares, endangering the way of life for over 1000 million people. Calculations show that approximately 2/5 of Earth's surface is dry land, with a limited fresh water supply, and a high percentage of these are eroded. Approximately 65% of the cultivable land has already lost a physical or a biological function.

In Latin America, indiscriminate use of agrochemicals for decades in agriculture has left residues, polluting the soil, surface and underground water. "*Pesticides are designed to kill, reduce and repel insects, weeds, rodents, mushrooms and other organisms that could harm public health and the nation's economies. When these chemical products are handled or disposed improperly, they can harm human health* ". "*The main risks linked to human health for being exposed chronically to small doses are related with cancer, birth defects, nervous and endocrine system disorders*". Statements from: Childhood Pesticides Poisoning: Information for Advocacy and Action", UNEP Chemicals, May 2004.

Developing our scientific research, we have found soils with absence of micro loads caused by the excessive use of agrochemicals used on them. Example: Rice growing in the Ibaqué area (Colombia). Tomato growing in Sinaloa (México). Soy growing in the Santa Fe province (Argentina), among other cases.

The environmental awareness, ecological knowledge, attitudes and values towards the environment have been growing within our communities. The problem with municipal, home, agricultural and livestock solid residues keeps growing and its production is excessive, the lack of separation from the source, incorrect disposal, lack of areas to handle them and lack of treatment or recovery. Among the main problems caused by the production of gases that pollute the atmosphere, leachates that pollute the soils, underground water, surface water and generation of sources for disease or vehicles for disease transmission. The current solid organic residues from any source are very different to the ones produced 20 years ago related to the accumulation of trace chemicals, this toxicity is directly related to the pesticide, herbicide and acaricide evolution, among others.

International organizations, such as the FAO (Food and Agriculture Organization) and the WHO (World Health Organization), have established the maximum allowed levels of pesticide ingestion, however, national authorities in each country are responsible for establishing the proper legislation and carefully monitoring its use and the amount of residue through adequate analytical controls.

This is a scientific research with nitrifying fungi, phosphorous solubilizers, antagonist to pathogens from Dr. Luis Orlando Castro's strain base, it is worth mentioning that the microorganisms used within this research were isolated originally by Dr. Luis Orlando Castro's group according to patent 11851 from Colombia, such strains have been worked with since 1984.

The fungi strains have been subjected to several stress stages using induced changes, adding traces to obtain chemical resistance to the synthetic pyrethroid bifenthrin (2-methyl biphenyl-3-ilmetil(2)-(1RS,3RS)-3-(2-chlorine 3,3,3-trifluoro propene)-2,2-dimethyl-cyclo-propane-carboxylate; alphanumeric code CA DPR Chem Code 2300.

CAS 82657-04-3. CIPAC 415. FMC 54800. PC Code 128825) and the thiodicarb carbamate (C10H18N4O4S3).

It is worth mentioning that the microorganism consortia here described have been deposited on Jul. 19, 2017 before the INIFAP at the National Center of Genetic Resources having an address of Boulevard de la Biodiversidad No. 400, Col Rancho Las Cruces, CP 47600, Tepatitlan de Morelos, Jalisco, Mexico, under accession number by the INTERNATIONAL DEPOSIT AUTHORITY: CM-CNRG TB46 (a deposit certificate is annexed). The consortium as deposited under accession number CM-CNRG TB46 includes the following microorganisms: *Paecilomyces sp., Trichoderma harzianum, Beauveria bassiana*, and *Metarhizium anisopliae*. More specifically, the consortium as deposited under accession number CM-CNRG TB46 consists of 25% *Paecilomyces sp.*, 25% *Trichoderma harzianum*, 25% *Beauveria bassiana*, and 25% *Metarhizium anisopliae*. Using these consortia for the production of liquid fertilizers, we are supplying a safe and effective product for agricultural use to control pests as an alternative to chemical insecticides and pesticides.

The following isolation protocol for resistant strains and the formation of the microbial consortium shows that every one of the strains was evolved towards attained resistance WITHOUT GENOME MANIPULATION for each organism. On the other hand, each strain was isolated and selected independently through consecutive strain growth increasing the synthetic pyrethroid concentrations, such as bifenthrin and carbamates such as thiodicarb.

Percentages for each microorganism belonging to the consortium vary from 20 to 30% of the CFU for each of the strains. Amount variability will depend of the soil characteristics and growth to which the consortium will be assigned.

PROCEDURE DESCRIPTION

During the entire research, for each of the fungi strains and on each of the stages, the following were performed:

a. Modifications to the growth media for each microorganism. Coloring to determine its size, form, cellular morphology, Gram staining and methyl violet to differentiate and view the hyphae or propagulus, mycelium, internal wall and cellular wall.

b. Growth charts and colony forming unit CFU/ml count per milliliter for the scheduled and defined times for this research.

c. The mycological strains were subject to direct lighting on each of the stages; starting with a soft light and increasing the intensity gradually through the stages; obtaining the desired adaptation.

d. Adaptation based in the humidity increase and temperature decrease.

Materials and Methods

Growth media: Liquids: Nutritious media. Solids: Agar, gel or silica gel, Nutrient agar, meat extract, yeast extract, sabouraud broth, malt extract, rice substrate, corn flour and some minerals.

Carbon sources: Organic: Peptone and sucrose (4-5%).

Nitrogen source: NH4 and nitrites.

Light source: Artificial light (low and medium intensity lamp).

Other growth elements: Water, hydrogen, oxygen, nitrogen, sulphur, phosphorous, potassium, magnesium, calcium, iron and sodium.

Trace elements: Cobalt, zinc, potassium, magnesium, molybdenum, sulphur, copper, manganese, carbamate (thiodicarb) and pyrethroid (bifenthrin).

Strains of sulphur sulubilizer fungi, antagonist to some pathogens:

a) *Paecilomyces* sp.

b) *Beauveria bassiana* c) *Trichoderma harzianum* d) *Metarhizium anisopliae*

Preparation for Stage Development

1. Glass material is sterilized in an autoclave.

2. The required amount of growth media is prepared with 3% rice broth (P/V), and 9% of a solution of molasses, sterilized at 121° C. for 15 minutes at a pressure of 15 lb.

3. Lethal dose (LD) applied to a hectare is established, for thiodicarb as well as bifenthrin. 10 Petri dishes are prepared with 0.1 LD of thiodicarb of bifenthrin. Dishes are incubated at 25° C. for 72 hours with cold light.

4. From the previous suspension with a known concentration, (107) the growth media is seeded with 1 ml, the pH adjustment is performed at 5.5 with a sterile 10 citric acid solution.

5. Stir at 110 rpm and 27 OC for 7 days.

6. The process is monitored controlling the variables, mainly the pH and biomass concentration, adjusting the pH to 5.5 during the entire process.

7. On the fourth day of the process, the foam formation is controlled with 1% soy oil and the stirring speed.

Methodology a. Petri dishes are placed inside the laminar flow chamber along with the diluted samples, to seed microorganisms in the dishes, a one ml sample of the strain is taken with an automated pipette, $10^{-1}$ and $10^{-2}$ solutions are performed, and each solution is homogenized.

b. Having the petri dishes with the sterile and cold growth media, it is homogenized with 6 right to left movements, 6 clockwise movements, 6 counterclockwise movements and 6 front to back movements over a flat horizontal surface until the inoculum is completely integrated into the media, stand until it solidifies and each dish is covered with parafilm to avoid contamination during incubation.

c. Dishes with thiodicarb and Bifenthrin are placed inside the incubator at 25° C. for 72 hours with a cold light lamp.

d. Inoculated dishes are incubated for 15 days, the product concentration impact is determined on mycelial growth, sporulation and germination (12 hours of incubation).

e. The residual impact of the product is reviewed after 7 days in the malt agar, dextrose and PDA agar media, enriched with minerals.

f. If there is no growth over 10%, the process is repeated until a mortality under 90% is obtained.

g. The colony diameter is determined using a graduated ruler, data is recorded subtracting the diameter of the seeded dish, from which the effect over the mycelial growth will be determined compared to the control (not poisoned MA, denominated as percentage of inhibition of radial growth (PIRG %).

h. Progress is recorded daily and after 7 days analysis of an acceptable coverage is performed, if not, the procedure is repeated as many times as required, later, a suspension of spores is prepared using the colony sweep method, the obtained suspension is placed in 160×20 mm tubes and 30 ml of sterile distilled water is added. After that, the suspension is stirred for 30 seconds in a Vortex tube mixer. The spore concentration is measured in a Newbawer Chamber and the results are reported in conidia per square millimeter.

i. From the 10 Petri dishes for each microorganism, the one with the lowest mortality rate is the one that will continue with the following study.

j. The study is performed again using this percentage until coverage increases and so on, the addition of thiodicarb and bifenthrin is alternated with the LD in intervals of 0.1 LD; all these experiments have been designed with the experimental strains and a control.

k. With the data obtained from the mycelial growth and sporulation, the percentage of inhibition of gradual growth is obtained, the data is transformed for its analysis with the expression 2 arc sin, and the sporulation through the equation Log 10(x+10). A two-way classification analysis of variance is applied and later the Turkey test is performed using a 5% probability.

Records

Characteristics for this procedure were recorded during all stages through the following indicators:
a. Growth speed
b. Percentage of inhibition measured in Number of CFU/mm
c. Percentage of poison resistance Stages Performed on Each Microorganism For each species, stages analyzing times required to cover the entire field were performed. Once this time was determined, they were left to rest for 10 days to be later subject to the following protocol:

Paecilomyces sp.

It is an entomopathogenic fungi, it can survive on organic matter in the soil and it is always present in the field, mainly in humid areas, it has a burgundy color. The conidiophores are erected, reaching from 400 to 600 µm growing individually (rarely in groups or synnemata) from the horizontal mycelium. Conidias are oval to fusiform from 2.5 to 3 µm long and from 2.0 to 2.2 µm wide.

Reproduction in the Laboratory

It is grown mainly in rice substrate with 47% humidity for 7 days at 28° C.

The growth media is prepared in an Erlenmeyer flask with PDA (Potato dextrose agar). A spore sample is taken from the fungi culture collection from the lab.

It is seeded in sterile Petri dishes, in potato dextrose agar and malt extract to maintain the colony pure. It is allowed to solidify for 2 to 3 minutes. After that, incubated at 24° C.+/−1 for 12-hour periods, alternating light/darkness for 15, 30 to 45 day periods.

Stages Performed in the Lab Using Paecilomyces sp.

During stages E-1 and E-2 (Stage 1 and Stage 2) 0.1 LD (0.0000175 gr) with a mortality rate from 60 to 62%. (On stage 2, the same concentration of thiodicarb is used to strengthen the growth of resistant strains). The resistant strains are transferred to solid growth media with 0.2 LD (0.000035 gr) of thiodicarb (E-3 and E-4, again on E-4 the same concentration of thiodicarb is used to strengthen the growth of resistant strains) with a mortality between 58 to 60%. At the end of stage E-4, organisms have been selected for 206 days.

Stages E-5 and E-6 are submitted to the first addition of bifenthrin; 0.1 LD (0.00000006 gr) of bifenthrin are added, with a mortality rate from 55 to 58% (in the same way as the previous case, E-6 is used to strengthen the growth of resistant strains). On stages E-7 and E-8 bifenthrin is increased to 0.2 LD (0.00000012 gr) with a 51 to 53% mortality rate. At the end of E-8 (growth strengthening stage for the resistant strains) the adaptation process reaches 384 days.

On stages E-9 y E-10, 0.3 LD (0.000053 gr) of thiodicarb are added, with a mortality rate from 50 to 48%. (The same way as in previous stages, E-10 is used to strengthen the growth of resistant strains). On stages E-11 and E-12 0.4 LD (0.000070 gr) of thiodicarb are added, with a mortality rate from 47 to 48%. At the end of stage E-12 (growth strengthening stage for the resistant strains) the selection process reaches 540 days.

On stages E-13 and E-14, 0.3 LD (0.00000018 gr) of bifenthrin are added, with a mortality rate from 45 to 44%. On stages E-15 and E-16, thiodicarb is increased to 0.4 LD (0.00000024 gr) with a 42 to 44% mortality rate. At the end of stage 16 (growth strengthening stage for the resistant strains) the selection process reaches 687 days.

On stages E-17 and E-18, 0.5 LD (0.000087 gr) of thiodicarb are added, with a mortality rate from 40 to 42% (The same way as in previous stages, E-18 is used to strengthen the growth of resistant strains). On stages E-19 and E-20, 0.6 LD (0.00011 gr) of thiodicarb are added, with a mortality rate from 38 to 42%. At the end of stage E-20 (growth strengthening stage for the resistant strains) the selection process reaches 823 days.

On stages E-21 and E-22, 0.5 LD (0.00000030 gr) of bifenthrin are added, with a mortality rate from 30 to 36% (The same way as in previous stages, E-22 is used to strengthen the growth of resistant strains). On stages E-23 and E-24, thiodicarb is increased to 0.6 LD (0.00000036 gr) with a mortality rate from 27 to 31%. At the end of stage 24 (growth strengthening stage for the resistant strains) the selection process reaches 935 days.

On stages E-25 and E-26, 0.7 LD (0.00012 gr) of thiodicarb are added, with a mortality rate from 25 to 23% (The same way as in previous stages, E-26 is used to strengthen the growth of resistant strains). On stages E-27 and E-28, 0.8 LD (0.00014 gr) of thiodicarb are added, with a mortality rate from 18 to 21%. At the end of stage E-28 (growth strengthening stage for the resistant strains) the selection process reaches 1032 days.

On stages E-29 and E-30, 0.7 LD (0.00000042 gr) of bifenthrin are added, with a mortality rate from 12 to 15% (The same way as in previous stages, E-30 is used to strengthen the growth of resistant strains). On stages E-31 and E-32, thiodicarb is increased to 0.8 LD (0.00000048 gr) with a mortality rate from 8 to 10%. At the end of stage 232 (growth strengthening stage for the resistant strains) the selection process reaches 1112 days.

On stages E-33 and E-34, 0.9 LD (0.00016 gr) of thiodicarb are added, with a mortality rate of 8% (The same way as in previous stages, E-34 is used to strengthen the growth of resistant strains). On stages E-35 and E-36, 1 LD (0.00018 gr) of thiodicarb are added, with a mortality rate of 15%. At the end of stage E-36 (growth strengthening stage for the resistant strains) the selection process reaches 1177 days.

On stages E-37 and E-38, 0.9 LD (0.00016 gr) of bifenthrin are added, with a mortality rate of 10% (The same way as in previous stages, E-38 is used to strengthen the growth of resistant strains). On stages E-39 and E-40, thiodicarb is increased to 1 LD (0.00018 gr) with a mortality rate of 5%. At the end of stage 40 (growth strengthening stage for the resistant strains) the selection process reaches 1223 days.

TABLE NO. 1

Comparative Table, Initial and Final Characteristics
SELECTIVE PROCESS CHARACTERISTICS *Paecilomyces* sp.

| PARAMETER | INITIAL | FINAL |
| --- | --- | --- |
| Ph | 7.0 | 7.0 |
| Humidity | 35% | 70% |
| Respiration | Aerobic | Aerobic |
| Temperature | 24 a 28° C. | 24 a 28° C. |
| Size | 80 to 250 μm in diameter | 80 to 250 μm in diameter |
| Resistant to: | Undetectable | Resistant to 1 LD of thiodicarb and bifenthrin |

*Beauveria bassiana*

It is an ascomycete mytosporic fungi that grows naturally in soils, with heterotrophic eukaryotic entomopathogen mycelium with chitinous cells. Its entomopathogenic ability allows insect parasitation. Its structure is formed by septated hyphae. The oval to fusiform conidia, from 2.5 to 3 μm long and from 2.0 to 2.5nμm wide. Spores are spherical and slightly oval with a whitish color. It grows on PDA in the lab in approximately 7 days at 8° C.

Stages Performed in the Lab Using *Beauveria bassiana*

Stages begin with the conditions in its natural habitat: pH—7.0 a 7.5, Humidity: 30 to 40% and humidity is increased up to 70% and a Temperature from 28 to 30° C., maintained during all the research term. These conditions are the starting point to adapt the strain to thiodicarb (carbamate) and bifenthrin (pyrethroid). During all stages, we will be using a cold light lamp to adapt the microorganism to sunlight.

To adapt this microorganism, 56 stages were performed, beginning the process with the conventional growth media. During stages E-1 and E-2 (Stage 1 and Stage 2) 0.1 LD (0.0000175 gr) of thiodicarb are added maintaining 32% humidity, with mortality rate of 73% (On stage 2, the same concentration of thiodicarb is used to strengthen the growth of resistant strains). The resistant strains are transferred to solid growth media with 0.2 LD (0.000035 gr) of thiodicarb (E-3 and E-4, again on E-4 the same concentration of thiodicarb is used to strengthen the growth of resistant strains) with a 73-79% mortality rate. At the end of stage E-4, organisms have been selected for 281 days.

Stages E-5 and E-6 are submitted to the first addition of bifenthrin; 0.1 LD (0.00000006 gr) of bifenthrin are added, with a 71 to 70% mortality rate (in the same way as the previous case, E-6 is used to strengthen the growth of resistant strains). On stages E-7 and E-8 bifenthrin is increased to 0.2 LD (0.00000012 gr) with a mortality rate from 68 to 65%. At the end of E-8 (growth strengthening stage for the resistant strains) the adaptation process reaches 547 days.

On stages E-9 and E-10, 0.3 LD (0.000053 gr) of thiodicarb are added, with a mortality rate from 66 to 65%. (The same way as in previous stages, E-10 is used to strengthen the growth of resistant strains). On stages E-11 and E-12 0.4 LD (0.000070 gr) of thiodicarb are added, with a mortality rate from 62 to 59%. At the end of stage E-12 (growth strengthening stage for the resistant strains) the selection process reaches 796 days.

On stages E-13 and E-14, 0.3 LD (0.00000018 gr) of bifenthrin are added, with a mortality rate from 57 to 55% (The same way as in previous stages, E-14 is used to strengthen the growth of resistant strains). On stages E-15 and E-16, thiodicarb is increased to 0.4 LD (0.00000024 gr) with a mortality rate from 53 to 50%. At the end of stage 16 (growth strengthening stage for the resistant strains) the selection process reaches 1036 days.

On stages E-17 and E-18, 0.5 LD (0.000087 gr) of thiodicarb are added, with a mortality rate from 51 to 49% (The same way as in previous stages, E-18 is used to strengthen the growth of resistant strains). On stages E-19 and E-20, 0.6 LD (0.00011 gr) of thiodicarb are added, with a mortality rate from 47 to 44%. At the end of stage E-20 (growth strengthening stage for the resistant strains) the selection process reaches 1245 days.

On stages E-21 and E-22, 0.5 LD (0.00000030 gr) of bifenthrin are added, with a mortality rate from 43 to 40% (The same way as in previous stages, E-22 is used to strengthen the growth of resistant strains). On stages E-23 and E-24, thiodicarb is increased to 0.6 LD (0.00000036 gr) with a mortality rate from 40 to 38%. At the end of stage 24 (growth strengthening stage for the resistant strains) the selection process reaches 1430 days.

On stages E-25 and E-26, 0.7 LD (0.00012 gr) of thiodicarb are added, with a mortality rate of 23% (The same way as in previous stages, E-26 is used to strengthen the growth of resistant strains). On stages E-27 and E-28, 0.8 LD (0.00014 gr) of thiodicarb are added, with a mortality rate from 34 to 33%. At the end of stage E-28 (growth strengthening stage for the resistant strains) the selection process reaches 1595 days.

On stages E-29 and E-30, 0.7 LD (0.00000036 gr) of bifenthrin are added, with a mortality rate from 32 to 30% (The same way as in previous stages, E-30 is used to strengthen the growth of resistant strains). On stages E-31 and E-32, thiodicarb is increased to 0.8 LD (0.00000042 gr) with a mortality rate from 30 to 28%. At the end of E-32 (growth strengthening stage for the resistant strains) the selection process reaches 1729 days.

On stages E-33 and E-34, 0.9 LD (0.00016 gr) of thiodicarb are added, with a mortality rate from 28 to 27% (The same way as in previous stages, E-34 is used to strengthen the growth of resistant strains). On stages E-35 and E-36, 1 LD (0.00018 gr) of thiodicarb are added, with a mortality rate of 26%. At the end of stage E-36 (growth strengthening stage for the resistant strains) the selection process reaches 1845 days.

On stages E-37 and E-38, 0.9 LD (0.00000042 gr) of bifenthrin are added, with a mortality rate from 27 to 26% (The same way as in previous stages, E-38 is used to strengthen the growth of resistant strains). On stages E-39 and E-40, thiodicarb is increased to 1 LD (0.00000048 gr) decreasing mortality rate from 25 to 24%. At the end of stage 40 the selection process reaches 1952 days.

On stages E-41 and E-42, 1.1 LD (0.0002 gr) of thiodicarb are added, with a mortality rate from 23 to 22% (The same way as in previous stages, E-42 is used to strengthen the growth of resistant strains). On stages E-43 and E-44, 1.2 LD (0.00022 gr) of thiodicarb are added, with a mortality rate of 20%. At the end of stage E-28 (growth strengthening stage for the resistant strains) the selection process reaches 2040 days.

On stages E-45 and E-46, 1.1 LD (0.00000054 gr) of bifenthrin are added, with a mortality rate from 20 to 28% (The same way as in previous stages, E-46 is used to strengthen the growth of resistant strains). On stages E-47 and E-48, thiodicarb is increased to 0.8 LD (0.00000060 gr) with a mortality rate from 16 to 14%. At the end of E-48 the selection process reaches 2110 days.

On stages E-49 and E-50, 1.1 LD (0.00024 gr) of thiodicarb are added, with a mortality rate of 14% (The same way as in previous stages, E-50 is used to strengthen the growth of resistant strains). On stages E-51 and E-52, 1.2 LD (0.00026 gr) of thiodicarb are added, with a mortality rate of 11%. At the end of stage E-52 (growth strengthening stage for the resistant strains) the selection process reaches 2198 days.

On stages E-53 and E-54, 1.2 LD (0.00000066 gr) of bifenthrin are added, with a mortality rate of 8% (The same way as in previous stages, E-54 is used to strengthen the growth of resistant strains). On stages E-55 and E-56, thiodicarb is increased to 1.3 LD (0.00000072 gr) with a mortality rate of 8%. At the end of E-56 (growth strengthening stage for the resistant strains) the selection process reaches 2268 days.

TABLE NO. 2

Comparative Table, Initial and Final Characteristics
SELECTIVE PROCESS CHARACTERISTICS *Bacillus megaterium*

| PARAMETER | INITIAL | FINAL |
|---|---|---|
| Ph | 7.0 | 7.0 |
| Humidity | 35% | 70% |
| Respiration | Aerobic | Aerobic |
| Temperature | 24-28° C. | 24-28° C. |
| Size | 1.0 × 3.0 μm | 1.0 × 3.0 μm |
| Measurements | 80 to 250 μm in diameter | 80 to 250 μm in diameter |
| Resistant to: | Organochlorinated, organic phosphorus compounds and mercury | 1 LD of thiodicarb and bifenthrin |

*Trichoderma harzianum*

It is a fungus that can be found in different organic matter, soils and in different environmental conditions, for which it is easy to adapt and propagate; prefer an acid pH from 4 to 4.5 and high humidity. This fungus generates toxins and antibiotics. Its mycelium has a whitish color, although it turns dark green over time and after sporulation; has several perpendicular ramifications, groups from 2 to 3 branches with pyramidal appearance; abundant conidia production, from 5 to 10 μm long and from 3.0 to 4.5 μm side. Grows in the laboratory on rice substrate with 47% humidity and at 28° C. for a 7-day period, in the presence of constant light.

Stages Performed in the Lab for *T. harzianum*

Procedures begin with the conditions in its natural habitat: Humidity: 30 to 40% and humidity is increased up to 70% and a Temperature from 28 to 30° C., maintained during all the research term. pH from 7.0 to 7.5. These conditions are the starting point to adapt the strain to thiodicarb and bifenthrin.

To adapt this microorganism, 56 stages were performed, beginning the process with the conventional growth media. During stages E-1 and E-2 (Stage 1 and Stage 2) 0.1 LD (0.0000175 gr) of thiodicarb. After incubation a slow growth is seen for the first 72 hours. Until day 68 of incubation mortality rate is at 82% and on stage E-2 at 85%. The remaining 83% is maintained for 10 days under daily observation to continue with the microorganism adaptation. Habitat temperature and humidity are maintained. (On stage 2, the same concentration of thiodicarb is used to strengthen the growth of resistant strains). The resistant strains are transferred to solid growth media with 0.2 LD (0.000035 gr) of thiodicarb (E-3 and E-4, again on E-4 the same concentration of thiodicarb is used to strengthen the growth of resistant strains) with a mortality rate of 83 to 82%. At the end of stage E-4, organisms have been selected for 396 days.

Stages E-5 and E-6 are submitted to the first addition of bifenthrin; 0.1 LD (0.00000006 gr) of bifenthrin are added, with a mortality rate from 83 to 82% (in the same way as the previous case, E-6 is used to strengthen the growth of resistant strains). On stages E-7 and E-8 bifenthrin is increased to 0.2 LD (0.00000012 gr) with a mortality rate from 81 to 80%. At the end of E-8 (growth strengthening stage for the resistant strains) the adaptation process reaches 766 days.

On stages E-9 and E-10, 0.3 LD (0.000053 gr) of thiodicarb are added, with a mortality rate from 78 to 76%. (The same way as in previous stages, E-10 is used to strengthen the growth of resistant strains). On stages E-11 and E-12 0.4 LD (0.000070 gr) of thiodicarb are added, with a mortality rate of 75%. At the end of stage E-12 (growth strengthening stage for the resistant strains) the selection process reaches 1124 days.

On stages E-13 and E-14, 0.3 LD (0.00000018 gr) of bifenthrin are added, with a mortality rate from 73 to 70% (The same way as in previous stages, E-14 is used to strengthen the growth of resistant strains). On stages E-15 and E-16, thiodicarb is increased to 0.4 LD (0.00000024 gr) with a mortality rate of 69%. At the end of stage 16 (growth strengthening stage for the resistant strains) the selection process reaches 1368 days.

On stages E-17 and E-18, 0.5 LD (0.000087 gr) of thiodicarb are added, with a mortality rate from 69 to 67% (The same way as in previous stages, E-18 is used to strengthen the growth of resistant strains). On stages E-19 and E-20, 0.6 LD (0.00011 gr) of thiodicarb are added, with a mortality rate of 66%. At the end of stage E-20 (growth strengthening stage for the resistant strains) the selection process reaches 1723 days.

On stages E-21 and E-22, 0.5 LD (0.00000030 gr) of bifenthrin are added, with a mortality rate of 65% (The same way as in previous stages, E-22 is used to strengthen the growth of resistant strains). On stages E-23 and E-24, thiodicarb is increased to 0.6 LD (0.00000036 gr) with a mortality rate 65 to 63%. At the end of stage 24 (growth strengthening stage for the resistant strains) the selection process reaches 1975 days.

On stages E-25 and E-26, 0.7 LD (0.00012 gr) of thiodicarb are added, with a mortality rate of 60% (The same way as in previous stages, E-26 is used to strengthen the growth of resistant strains). On stages E-27 and E-28, 0.8 LD (0.00014 gr) of thiodicarb are added, with a mortality rate from 58 to 56%. At the end of E-28 (growth strengthening stage for the resistant strains) the selection process reaches 2203 days.

On stages E-29 and E-30, 0.7 LD (0.00000036 gr) of bifenthrin are added, with a mortality rate from 55 to 52% (The same way as in previous stages, E-30 is used to strengthen the growth of resistant strains). On stages E-31 and E-32, thiodicarb is increased to 0.8 LD (0.00000042 gr) with a mortality rate from 48 to 44%. At the end of E-32 (growth strengthening stage for the resistant strains) the selection process reaches 23974 days.

On stages E-33 and E-34, 0.9 LD (0.00016 gr) of thiodicarb are added, with a mortality rate from 42 to 40% (The same way as in previous stages, E-34 is used to strengthen the growth of resistant strains). On stages E-35 and E-36, 1 LD (0.00018 gr) of thiodicarb are added, with a mortality rate from 38 to 35%. At the end of stage E-36 (growth strengthening stage for the resistant strains) the selection process reaches 2556 days.

On stages E-37 and E-38, 0.9 LD (0.00000042 gr) of bifenthrin are added, with a mortality rate from 24 to 22% (The same way as in previous stages, E-38 is used to strengthen the growth of resistant strains). On stages E-39 and E-40, thiodicarb is increased to 1 LD (0.00000048 gr) decreasing mortality 28 to 25%. At the end of stage 40 the selection process reaches 2686 days; 7.4 years of research.

On stages E-41 and E-42, 1.1 LD (0.0002 gr) of thiodicarb are added, with a mortality rate from 24 to 22% (The same way as in previous stages, E-42 is used to strengthen the growth of resistant strains). On stages E-43 and E-44, 1.2 LD (0.00022 gr) of thiodicarb are added, with a mortality rate of 18%. At the end of stage E-28 (growth strengthening stage for the resistant strains) the selection process reaches 2805 days.

On stages E-45 and E-46, 1.1 LD (0.00000054 gr) of bifenthrin are added, with a mortality rate from 20 to 18% (The same way as in previous stages, E-46 is used to strengthen the growth of resistant strains). On stages E-47 and E-48, thiodicarb is increased to 0.8 LD (0.00000060 gr) with a mortality rate of 14%. At the end of E-48 the selection process reaches 2914 days.

On stages E-49 and E-50, 1.1 LD (0.00024 gr) of thiodicarb are added, with a mortality rate of 10% (The same way as in previous stages, E-50 is used to strengthen the growth of resistant strains). On stages E-51 and E-52, 1.2 LD (0.00026 gr) of thiodicarb are added, with a mortality rate of 8%. At the end of stage E-52 (growth strengthening stage for the resistant strains) the selection process reaches 2198 days.

On stages E-53 and E-54, 1.2 LD (0.00000066 gr) of bifenthrin are added, with a mortality rate of 10% (The same way as in previous stages, E-54 is used to strengthen the growth of resistant strains). On stages E-55 and E-56, thiodicarb is increased to 1.3 LD (0.00000072 gr) with a mortality rate of 8%. At the end of E-56 (growth strengthening stage for the resistant strains) the selection process reaches 3001 days.

TABLE NO. 3

Comparative Table, Initial and Final Characteristics
DEVELOPMENT CHARACTERISTICS *Trichoderma harzianum*

| PARAMETER | INITIAL | FINAL |
|---|---|---|
| pH | 2 to 4.5 | 7 |
| Humidity | 60% | 70% |
| Respiration | Aerobic | Aerobic |
| Temperature | 24 to 27° C. | 25 to 27° C. |
| Resistant to: | Organochlorinated, organic phosphorus compounds and mercury | 1 LD of thiodicarb and bifenthrin |
| Size | 5 × 10 μm in diameter | 6 × 10 μm in diameter |
| Resistant to: | N/A | 1.3 LD of thiodicarb and bifenthrin |

*Metarhizium anisopliae*

This fungi is characterized by smooth hyphae, septated conidia predominantly cylindrical, grouped, green uninucleate with rounded endings, the average size was 6 mm long and 2.5 mm wide.

The natural habitat for this fungi are ground larvae, commonly known as grub worms, scientific name Phillophaga, on sugar cane farmlands where this pest is present, causing significant damage to the crops.

This fungi is characterized by smooth hyphae, septated conidia predominantly cylindrical, grouped, green uninucleate with rounded endings, the average size was 6 mm long and 2.5 mm wide.

STAGES PERFORMED IN THE LAB FOR *Metarhizium anisopliae*

Stages begin with the conditions in its natural habitat. It grows in the lab on rice substrate with 47% humidity for approximately 7 days at 28° C., and constant exposure to light on PDA for approximately 7 days at 28° C. These conditions are the starting point to adapt the strain to thiodicarb and bifenthrin. During all stages a cold light lamp will be used to adapt the microorganism to sunlight.

To adapt this microorganism, 40 stages were performed, beginning the process with the special growth media, which was enriched with minerals. During stages E-1 and E-2 (Stage 1 and Stage 2) 0.1 LD (0.0000175 gr) of thiodicarb. After incubation a slow growth is seen for the first 72 hours. Until day 45 of incubation mortality rate is rate is from 58 to 56%. The remaining 40% is maintained for 10 days under daily observation to continue with the microorganism adaptation. Habitat temperature and humidity are maintained. (On stage 2, the same concentration of thiodicarb is used to strengthen the growth of resistant strains). The resistant strains are transferred to solid growth media with 0.2 LD (0.000035 gr) of thiodicarb (E-3 and E-4, again on E-4 the same concentration of thiodicarb is used to strengthen the growth of resistant strains) with a mortality rate of 55%. At the end of stage E-4, organisms have been selected for 220 days.

Stages E-5 and E-6 are submitted to the first addition of bifenthrin; 0.1 LD (0.00000006 gr) of bifenthrin are added, with a mortality rate from 54 to 52% (in the same way as the previous case, E-6 is used to strengthen the growth of resistant strains). On stages E-7 and E-8 bifenthrin is increased to 0.2 LD (0.00000012 gr) with a mortality rate from 50 to 48%. At the end of E-8 (growth strengthening stage for the resistant strains) the adaptation process reaches 421 days.

On stages E-9 and E-10, 0.3 LD (0.000053 gr) of thiodicarb are added, with a mortality rate from 52 to 48%. (The same way as in previous stages, E-10 is used to strengthen the growth of resistant strains). On stages E-11 and E-12 0.4 LD (0.000070 gr) of thiodicarb are added, with a mortality rate from 45 to 43%. At the end of stage E-12 (growth strengthening stage for the resistant strains) the selection process reaches 606 days.

On stages E-13 and E-14, 0.3 LD (0.00000018 gr) of bifenthrin are added, with a mortality rate from 40 to 38% (The same way as in previous stages, E-14 is used to strengthen the growth of resistant strains). On stages E-15 and E-16, thiodicarb is increased to 0.4 LD (0.00000024 gr) with a mortality rate from 38 to 35%. At the end of stage 16 (growth strengthening stage for the resistant strains) the selection process reaches 754 days.

On stages E-17 and E-18, 0.5 LD (0.000087 gr) of thiodicarb are added, with a mortality rate from 34 to 33% (The same way as in previous stages, E-18 is used to strengthen the growth of resistant strains). On stages E-19 and E-20, 0.6 LD (0.00011 gr) of thiodicarb are added, with a mortality rate from 33 to 31%. At the end of stage E-20 (growth strengthening stage for the resistant strains) the selection process reaches 874 days.

On stages E-21 and E-22, 0.5 LD (0.00000030 gr) of bifenthrin are added, with a mortality rate from 29 to 25% (The same way as in previous stages, E-22 is used to strengthen the growth of resistant strains). On stages E-23 and E-24, thiodicarb is increased to 0.6 LD (0.00000036 gr) with a mortality rate from 22 to 20%. At the end of stage 24 (growth strengthening stage for the resistant strains) the selection process reaches 978 days.

On stages E-25 and E-26, 0.7 LD (0.00012 gr) of thiodicarb are added, with a mortality rate from 18 to 15% (The same way as in previous stages, E-26 is used to strengthen the growth of resistant strains). On stages E-27 and E-28, 0.8 LD (0.00014 gr) of thiodicarb are added, with a mortality rate from 12 to 11%. At the end of stage E-28 (growth strengthening stage for the resistant strains) the selection process reaches 1060 days of adaptation.

On stages E-29 and E-30, 0.7 LD (0.00000036 gr) of bifenthrin are added, with a mortality rate from 11 to 9% (The same way as in previous stages, E-30 is used to strengthen the growth of resistant strains). On stages E-31 and E-32, thiodicarb is increased to 0.8 LD (0.00000042 gr) with a mortality rate from 7 to 5%. At the end of E-32 (growth strengthening stage for the resistant strains) the selection process reaches 1125 days.

On stages E-33 and E-34, 0.9 LD (0.00016 gr) of thiodicarb are added, with a mortality rate of 15% (The same way as in previous stages, E-34 is used to strengthen the growth of resistant strains). On stages E-35 and E-36, 1 LD (0.00018 gr) of thiodicarb are added, with a mortality rate of 15%. At the end of stage E-36 (growth strengthening stage for the resistant strains) the selection process reaches 2556 days of adaptation.

On stages E-37 and E-38, 0.9 LD (0.00000042 gr) of bifenthrin are added, with a mortality rate from 24 to 22% (The same way as in previous stages, E-38 is used to strengthen the growth of resistant strains). On stages E-39 and E-40, thiodicarb is increased to 1 LD (0.00000048 gr) decreasing mortality rate from 28 to 25%. At the end of stage 40 the selection process reaches 2686 days.

TABLE NO. 4

Comparative Table, Initial and Final Characteristics
DEVELOPMENT CHARACTERISTICS *Metarhizium anisopliae*

| PARAMETER | INITIAL | FINAL |
|---|---|---|
| pH | 2-4.5 | 7.0 |
| Humidity | 60% | 60% |
| Respiration | Aerobic | Aerobic |
| Temperature | 24-27° C. | 25-27° C. |
| Resistant to: | N/A | 1.3 LD of thiodicarb and bifenthrin |

REFERENCES

Castro, L. 1997. Mixture for the biodegradation of organic matter consisting of a specific growth media and microorganisms adapted to air and the seeding process. U.S. Pat. No. 26,662 issued by the Economic development Ministry of Colombia.

Castro, L. 2006. Composite of microorganisms adapted to biodegrade the Organic portion contained in solid residues and the preparation process. Patent No. PA/2006/003777, issued by the IMPI. Mexico. (Issued Apr. 27, 2017)

Orozco J. C, Martinez P. Test of the seeding of nitrogen-fixing non-symbiotic microorganisms isolated from the rhizosphere of *Pinus patula* in Colombia. Alexander von Humboldt Biological Research Institute, La Florida Forest Station, Cota. BOSQUE 30(2): 70-77, Cundinamarca-Colombia. 2009.

Cuervo J. Isolation and Characterization of the *Bacillus* spp as biological nitrogen fixers and phosphate solubilizers in two samples of commercial biofertilizers. Degree work. Agricultural and livestock microbiology. Bogotá-Colombia, 2010.

Kabir, M. and D. Faure. 1995. Identification of Azospirillum by oligonucleotide probes after isolation from soil and *Sourghum rizoplan* contaminated or not by the parasitic plant Siriga. Advances in Applied Microbiology. 35. 195-253.

Kabir, M.; Faure, D.; Heulin, T.; Achoawk, W.; and R. Bally. 1995. Oligonucleotide probes based on 165 Rrna sequences for the identification of four Azospirillum species. Can. J. Microbiol. 41: 1081-1087.

Validation of the Publication of New Names and New Combinations. Previously Effectively Published Outside the USB. List no. 51. International Journal of Systematic Bacteriology, 1994.

Invention Summary

This invention provides the methodology to make a consortium of beneficial fungi resistant to carbamates contained in thiodicarb and the synthetic pyrethroid traces contained in bifenthrin.

During the development of this research, performed in a time period over 5 years, the strains are subject to a physical media change, adapting them to withstand increasing concentrations of thiodicarb and bifenthrin.

This compound enriches and increases the beneficial microorganism concentration, generating high-quality liquid biofertilizers, suitable to be used in agricultural production, in the soil conservation and recovery, complying with parameters established by sustainable organic agriculture where nature and the environment are maintained, recovered and used without causing negative impact.

The invention claimed is:

1. A consortium of microorganisms including fungi and bacteria, wherein the microorganisms of the consortium are initially exposed to a series of increasing fractions of a lethal dose of thiodicarb, subsequently exposed to a series of increasing fractions of a lethal dose of bifenthrin, wherein subsequent to the exposures of thiodicarb and bifenthrin, the microorganisms of the consortium are resistant to 1 to 1.3 times the lethal dose of thiodicarb and bifenthrin, wherein the consortium is able to be seeded in liquid, foliar, edaphic or irrigation systems, wherein the consortium was deposited with the National Center of Genetic Resources (CM-CNRG) under accession number CM-CNRG TB46.

2. The consortium according to claim 1, wherein the consortium is operable to act as any of a biofertilizer, biopesticide and biofungicide on crops, either under edaphic or foliar conditions.

3. The consortium according to claim 1, wherein the consortium is operable to grow and conduct metabolic processes in a presence of sunlight, either under edaphic or foliar conditions.

4. A consortium of microorganisms including fungi and bacteria, wherein the microorganisms of the consortium are exposed to increasing first fractions of a lethal dose of thiodicarb, subsequently exposed to increasing first fractions of a lethal dose of bifenthrin, subsequently exposed to increasing second fractions of a lethal dose of thiodicarb, wherein the second fractions of a lethal dose of thiodicarb are greater than the first fractions of a lethal dose of thiodicarb, subsequently exposed to increasing second fractions of a lethal dose of bifenthrin, wherein the second fractions of a lethal dose of bifenthrin are greater than the first fractions of a lethal dose of bifenthrin, subsequently exposed to increasing third fractions of a lethal dose of thiodicarb, wherein the third fractions of a lethal dose of thiodicarb are greater than the second fractions of a lethal dose of thiodicarb, subsequently exposed to increasing third fractions of a lethal dose of bifenthrin, wherein the third fractions of a lethal dose of bifenthrin are greater than the second fractions of a lethal dose of bifenthrin, subsequently exposed to increasing fourth fractions of a lethal dose of thiodicarb, wherein the fourth fractions of a lethal dose of thiodicarb are greater than the third fractions of a lethal dose of thiodicarb, subsequently exposed to increasing fourth fractions of a lethal dose of bifenthrin, wherein the fourth fractions of a lethal dose of bifenthrin are greater than the third fractions of a lethal dose of bifenthrin, subsequently exposed to increasing fifth fractions of a lethal dose of thiodicarb, wherein the fifth fractions of a lethal dose of thiodicarb are greater than the fourth fractions of a lethal dose of thiodicarb, and subsequently exposed to increasing fifth fractions of a lethal dose of bifenthrin, wherein the fifth fractions of a lethal dose of bifenthrin are greater than the fourth fractions of a lethal dose of bifenthrin, wherein subsequent to the first through fifth exposures of thiodicarb and the first through fifth exposures of bifenthrin, the microorganisms of the consortium are resistant to a lethal dose of thiodicarb and bifenthrin, wherein the consortium is operable to be seeded in liquid, foliar, edaphic or irrigation systems, wherein the consortium was deposited with the National Center of Genetic Resources (CM-CNRG) under accession number CM-CNRG TB46.

\* \* \* \* \*